(12) United States Patent
Harris

(10) Patent No.: US 7,951,393 B2
(45) Date of Patent: May 31, 2011

(54) KELOID THERAPY

(76) Inventor: Canaan Vernon Lavelle Harris, Houston, TX (US)

( * ) Notice: Subject to any disclaimer, the term of this patent is extended or adjusted under 35 U.S.C. 154(b) by 0 days.

(21) Appl. No.: 12/268,754

(22) Filed: Nov. 11, 2008

(65) Prior Publication Data

US 2009/0123520 A1    May 14, 2009

Related U.S. Application Data

(60) Provisional application No. 60/987,800, filed on Nov. 14, 2007.

(51) Int. Cl.
*A61K 9/00* (2006.01)
*A61P 17/02* (2006.01)

(52) U.S. Cl. ........................ 424/425; 424/484

(58) Field of Classification Search .......... None
See application file for complete search history.

(56) References Cited

U.S. PATENT DOCUMENTS

| | | | |
|---|---|---|---|
| 3,993,072 A | 11/1976 | Zaffaroni | |
| 5,073,202 A | 12/1991 | Wallach | |
| 5,563,153 A * | 10/1996 | Mueller et al. | 514/305 |
| 6,685,697 B1 | 2/2004 | Arenberg et al. | |
| 2005/0142162 A1 * | 6/2005 | Hunter et al. | 424/423 |

OTHER PUBLICATIONS

Chowdri et al. Keloids and hypertrophic scars: results with intraoperative and serial postoperative corticosteroid injection therapy, Aust. N.Z. J. Surg. 69, 655-59 (1999).*

Pharmacia & Upjohn Company; Gelfoam® absorbable gelatin powder from absorable gelatin sponge, USP package insert; revised Aug. 2003; Kalamazoo, MI.

Bristol-Myers Squibb Company; Kennlog® -40 Injection—triamcinolone acetonide injectable suspension, USP package insert; revised Nov. 2007; Princeton, NJ.

* cited by examiner

*Primary Examiner* — Jeffrey S. Lundgren
*Assistant Examiner* — Sara E Townsley
(74) *Attorney, Agent, or Firm* — Daniel N. Lundeen; Lundeen & Lundeen PLLC

(57) ABSTRACT

Therapeutic compositions, devices and protocols for the treatment of keloids and other abnormal scars with improved appearance and a much lower recurrence rate. A therapeutic drug delivery device comprises an injectable mixture of a fibroblast inhibitor such as corticosteroid and a slow release carrier such as milled gel sponge dispersed in a fluid medium such as biological saline. The composition can be injected perilesionally in the dermis following excision of the keloid or other scar tissue, to circumscribe the wound. The infiltration of the mixture around the wound can provide a slow release of the fibroblast inhibitor for an extended period of time until normal wound closure can dominate and keloid or abnormal scar recurrence is inhibited.

20 Claims, 3 Drawing Sheets

KELOID THERAPY

CROSS REFERENCE TO RELATED APPLICATION

This application is a nonprovisional of my earlier application U.S. 60/987,800, filed Nov. 14, 2007, and hereby claims priority thereto and the benefit thereof.

BACKGROUND OF THE INVENTION

Keloids are an example of abnormal scars that grow beyond the boundaries of the original skin injury site, and have the appearance of a raised amorphous growth, frequently associated with pruritus and pain. Histologically, keloids can be distinguished by the randomly organized collagen fibers in a dense connective tissue matrix, whereas in normal scars the collagen bundles are generally parallel to the skin surface. The most common keloid sites in the head and neck are the earlobes, mandibular border and posterior neck.

Abnormal scars also include spread scars and hypertrophic scars. Spread scars occur when a wound is not properly closed or secondary to original wound breakdown. Hypertrophic scars occur with a similar histology to keloid scars, but usually occur when the wound is under stress.

The pathophysiology of keloids and other abnormal scars is not well understood. A leading theory is that fibroblasts and myofibroblasts are responsible for depositing a dense extracellular matrix of collagen and glycosaminoglycans. Elevated fibronectin production has been reported by keloidal fibroblasts. Other theories include: an allergic immunoglobulin E (IgE)-mediated response, leading to a decreased percentage of mature cross-linked collagen and an increased fraction of soluble collagen; a deficiency in melanocyte-stimulating hormone (MSH) metabolism or an excess of MSH, noting that increases in MSH and subsequent keloid formation are associated with pregnancy and puberty; microvascular occlusion and subsequent hypoxia; elevated interleukin-6 (IL-6) expression; and insulinlike growth factor-1 (IGF-1) and IGF-1 receptor axis in the invasive activity of keloids.

Surgical, non-surgical and combined modality treatments have been used or proposed, with limited success; e.g. recurrence rates of 50-80% are accepted. One of the most common therapies known is cold-knife excision followed by intralesional steroid injection, usually 2-3 weeks postoperatively with a repeat injection in 3-4 weeks to delay wound healing and increase the likelihood of wound dehiscence. Corticosteroids work by inhibiting fibroblast growth and promoting collagen degradation. Triamcinolone suspension at 10 mg/mL is commonly used, although dexamethasone and cortisone have also been used. Higher triamcinolone concentrations to 40 mg/mL have been used for dense, recalcitrant keloids, but the risk of depigmentation and dermal atrophy are greater. Still, reported recurrence rates low.

More aggressive keloid treatment therapies have included radiation therapy, without statistical significance but a slightly lower recurrence rate. However, aggressive therapies such as radiation for treatment of benign conditions have potential disadvantages such as, for example, thyroid or salivary gland neoplasia which have a latency of 15-20 years.

SUMMARY OF THE INVENTION

The present invention is directed to therapeutic compositions, devices and protocols for the treatment of keloids with improved appearance and a much lower recurrence rate. It has been found that a therapeutic composition comprising an injectable mixture of a fibroblast inhibitor, such as corticosteroid in an embodiment, and a slow release carrier, such as milled gel sponge in an embodiment, dispersed in a fluid medium such as biological saline, can effectively inhibit keloid recurrence following excision of a recalcitrant keloid. In an embodiment, the composition can be injected perilesionally in the dermis following excision of the keloid or other scar tissue, to circumscribe the wound. The infiltration of the mixture around the wound can provide a slow release of the fibroblast inhibitor for an extended period of time to facilitate normal wound healing.

In one embodiment, the present invention provides a drug delivery device useful for inhibiting fibroblast growth or treating keloid scars, comprising an admixture of a fibroblast inhibitor, a particulated heterogeneous slow release matrix, and a carrier fluid. In embodiments, the fibroblast inhibitor can be a corticosteroid, preferably triamcinolone.

In an embodiment, the slow release matrix can be milled absorbable gelatin sponge. The fibroblast inhibitor can be interstitially disposed in the sponge, and the sponge can be dispersed in an excess of the viscous fluid. The viscous fluid can be biological saline solution, for example.

In an embodiment, the composition can be prepared by a method comprising admixing a corticosteroid suspension comprising an excess of water or saline with dehydrated gel sponge powder to hydrate the gel sponge and to dispose the corticosteroid in interstices of the gel sponge.

In a particular embodiment, the present invention provides a drug delivery device or system, comprising an admixture of an aqueous corticosteroid suspension and a particulated gel sponge, wherein the corticosteroid is disposed interstitially in the gel sponge and the gel sponge is dispersed in excess viscous liquid. In an embodiment, the drug delivery device is useful for inhibiting recurrence of surgically excised keloid scars.

In another particular embodiment, the present invention provides a powdered mixture of corticosteroid and gel sponge, which is hydratable with excess aqueous fluid to form an admixture of an aqueous corticosteroid suspension and a particulated gel sponge wherein the corticosteroid is disposed interstitially in the gel sponge and the gel sponge is dispersed in excess fluid.

In another particular embodiment, the present invention provides a sterile single-use container comprising the composition of any of the preceding embodiments. In an embodiment, the container can be a syringe. For example, the syringe can have a needle wherein the composition is injectable through the needle. The syringe can also have a sleeve associated with the needle and wherein a distal end of the needle extends beyond the sleeve to a distance of from 2 to 10 mm. Alternatively or additionally, the syringe can have a 5-30 mm first lateral spacing element associate with the sleeve, and/or a 1-2 cm second lateral spacing element associated with the sleeve.

In a further embodiment, the invention provides a method including perilesionally injecting the composition described above into the dermis adjacent to a wound. In an embodiment, the method has utility for extended time inhibition of fibroblast growth in a wound. The injections can be serially spaced to circumscribe the wound, for example. In an embodiment, the injections can be spaced from 5 to 30 mm from a margin of the wound and/or to a depth of from 2 to 10 mm. If desired, adjacent injections can be spaced apart by from 1 to 2 cm.

In another embodiment of the method, the adjacent injections can have abutting infiltration to circumscribe the wound. The method can be particularly beneficial when the wound is formed by surgical excision of a scar, such as a keloid, spread or hypertrophic scar or the like, preferably total scar excision and more preferably with reconstruction of the excision site prior to the serial injections.

DESCRIPTION OF THE INVENTION

Figure 1:
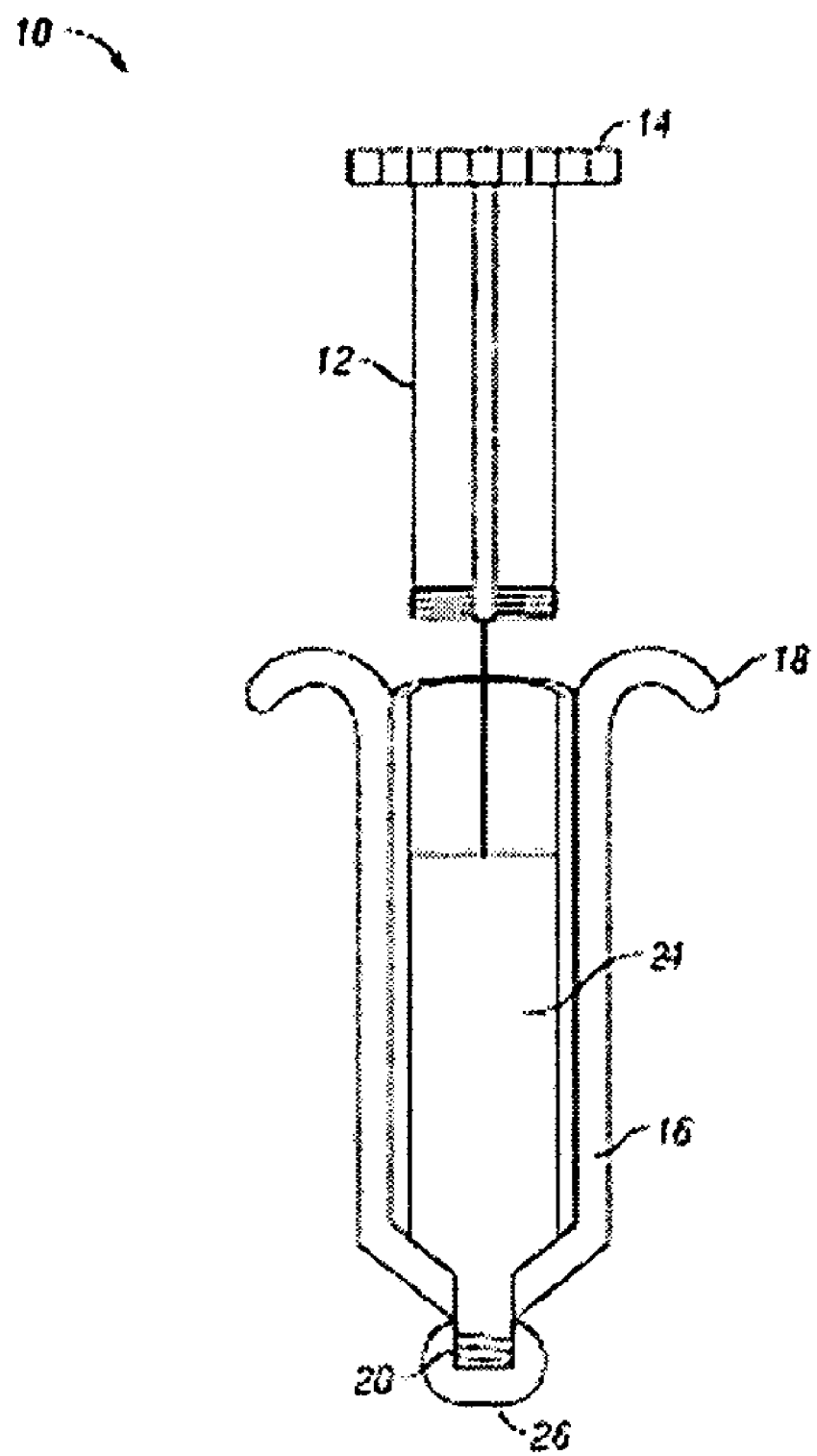
FIG. 1 is a partially exploded side sectional view of a syringe cylinder and plunger according to an embodiment of the invention.

The present invention is directed to therapeutic compositions, devices and protocols for the treatment of keloids and other abnormal scars with improved appearance and a much lower recurrence rate. Reference is made below to keloids as only one example of abnormal scars that can be treated according to various embodiments of the invention, for the purpose of illustration and clarity and not by way of limitation.

The invention is directed more specifically to an embodiment of a therapeutic composition comprising a mixture of a fibroblast inhibitor and a slow release carrier dispersed in a fluid medium. In one embodiment, preferably following excision of the keloid or other scar tissue, the therapeutic composition can be injected perilesionally in the dermis, preferably circumscribing the wound, to provide a slow release of the fibroblast inhibitor for an extended period of time.

In one embodiment, the fibroblast inhibitor is a corticosteroid such as triamcinoline, dexamethasone and cortisone. Free acid or base forms of the steroids can be used when they or their metabolites are biologically active, and the corresponding base or acid addition salts or esters can additionally or alternatively be used. Typical treatment concentrations for corticosteroids such as triamcinolone, dexamethasone or cortisone, or other fibroblast inhibitor, can be used, for example, 10 to 40 mg/mL triamcinolone, based on the volume of the corticosteroid suspension. In another embodiment other fibroblast growth inhibitors such as interferon can be used. The invention is discussed below using corticosteroid or steroid as an exemplary fibroblast growth inhibitor, and should not be construed as a limitation on the invention. Alternatively or additionally, a fluid such as water, saline or organic liquid, can be added to obtain the desired rheological characteristics for administration.

In one embodiment, the slow release carrier comprises a three-dimensional physical microstructure providing a matrix to hold the corticosteroid chemically and/or physically within interstices of the structure. The carrier can also be relatively biologically inert to minimize the risk of an excessive inflammatory or other adverse reaction. The carrier can be dispersible within a fluid so that the mixture can form a paste or gel with the fluid medium that can be injected through a needle, e.g. a 12 gauge (2.159 mm inside diameter) needle with a 5 or 10 ml syringe, into the perilesional dermis. Gelatin, crosslinked polysaccharides, polyacrylamide gels, polylactides, polyglycolides, resorbable nylon, and the like are contemplated.

In a preferred embodiment, the slow release carrier matrix is formed from water-swellable heterogeneous biopolymer particles or powder which is reconstituted with an injectable steroid suspension or solution. The steroid suspension or solution is mixed with the dehydrated biopolymer particles and the fluid from the suspension hydrates the biopolymer and carries the steroid into the interstices of the hydrated biopolymer. In an embodiment wherein the steroid is a particulated solid or gel, the interstices have pore openings to a surface of the gel structure that are sufficiently large to accommodate entry of the steroid particles. A slight excess of the steroid suspension is used so that the excess fluid can fluidize the biopolymer to the desired consistency for injection, e.g. a paste, or gel.

For example, the therapeutic composition or device can be formed by saturating GELFOAM absorbable gelatin powder with KENALOG triamcinoline suspension in biological saline in a weight ratio of suspension:powder of 3:1 or 4:1. GELFOAM powder and KENALOG suspension are commercially available. Briefly, GELFOAM powder is an absorbable gelatin powder comprising a water-insoluble, off-white, non-elastic, porous, pliable product prepared from purified pork skin gelatin as a fine dry heat-sterilized light powder prepared by milling absorbable gelatin sponge, which is able to hold within its interstices many times its weight of liquids. GELFOAM powder, when placed in soft tissues as a hemostatic agent, is usually absorbed completely in from 4 to 6 weeks. Below reference is made to the gel powder as a representative embodiment for the purposes of an example, and not by way of limitation.

According to an embodiment of the method of the invention, the composition is injected perilesionally, e.g. around the wound margins to inhibit keloid formation in an individual with a history of or otherwise susceptible to keloid formation, preferable following surgery or other wound trauma, especially following keloidal excision. The injection is in the peri scar region around wound, typically from 5 to 20 or 30 mm from the wound margin. The injection is into the dermis, preferably at a subcutaneous depth of from 2 to 10 mm or 2 to 5 mm. The needle can be provided with a sleeve wherein the extension of the needle from a distal end thereof can be used to control the depth of the injection. The needle or sleeve can also be provided with a lateral spacing element to consistently locate the injection site from the wound margin and/or adjacent injection sites. The extent of infiltration can be judged by the thickness of the dermis or the firmness of the skin after infiltration is complete. Palpation of the injection site post-injection can make the subdermal infiltrate disposition more uniform and laterally extensive. The injections can be repeated serially in injection sites spaced apart by from 1 to 2 or 5 cm so that the infiltration of adjacent injection sites preferably overlaps or abuts to circumscribe the wound. In general, the thinner the dermis, the less amount of infiltration that is used and the closer the injection site is located relative to the wound margin; for a thicker dermis adjacent the wound margin, the farther the injection site is laterally disposed and the greater the quantity of the injection volume that is infiltrated.

According to an embodiment of the device of the invention, the therapeutic composition can be supplied premixed as an injectable suspension of the consistency of paste in sterile vials or other containers and used with an appropriate needle and syringe into which it can be drawn prior to use. In another embodiment, the steroid and gelatin powder can be supplied in a premixed powder form that is anhydrous or only partially hydrated, which is preferably prepared by hydrating the gel powder with the steroid suspension in biological saline or water, followed by drying and milling the mixture so that the steroid is already interstitially located in the gel matrix. The premixed powder can then be reconstituted with water or biological saline and injected perilesionally as described above.

In another preferred embodiment, the therapeutic composition can be supplied in a preloaded, sterile syringe, with or without a needle. The preloaded syringe can be provided with a needle having a sleeve which provides a fixed length of needle protrusion corresponding to the injection depth for a specific dermal thickness. The preloaded syringe/needle combination can be labeled for injection parameters and/or appropriate dermal and wound characteristics for use, along with instructions or protocol. Alternatively, the syringe can be provided with an array of needles of different protrusion lengths and, optionally, appropriate labeling, or an array of different syringe/needle combinations can be provided, separately or in a unitary treatment package. In another preferred embodiment, the sleeves can have a diameter of the appropriate or recommended spacing from the wound margin, which can similarly include labeling for injection parameters and/or appropriate dermal and wound characteristics for use, along with instructions or protocol. Alternatively or additionally, the needle or sleeve can be provided with lateral spacing elements or rulers to determine spacing from the wound margin and/or an adjacent injection site.

The slow release of the steroid can in some cases cause suppressive changes over a 4 to 6 week period of the adenocorticoid system leading iatrogenic hypoadenocorticoid-type clinical presentation. In one embodiment, serum cortisol levels are monitored pre- and/or postoperatively over a 2- or 3-month period, e.g., weekly or biweekly beginning one month after treatment. In the event the cortisol levels descend, supplemental steroids such as prednisone or methylprednisolone can be administered on a tapered basis over a 3- to 6-week time period, for example. Care should also be exercised in the treatment of prepuberty females because some changes in menstrual cycle regularity may occur. Diabetic patients should be treated cautiously and monitored closely for serum glucose fluctuations. Other conditions that can be considered include rheumatic disorders, renal insufficiency, hepatic disorders, musculoskeletal degenerative disorders, osteoporosis, and the like conditions contraindicative for steroid or gel therapy. In one embodiment, allergic reaction to steroids or gel can be tested, before therapeutic use, by subcutaneous inoculation and observing for any wheal formation or other reaction at 24 to 48 hours.

Figure 2:
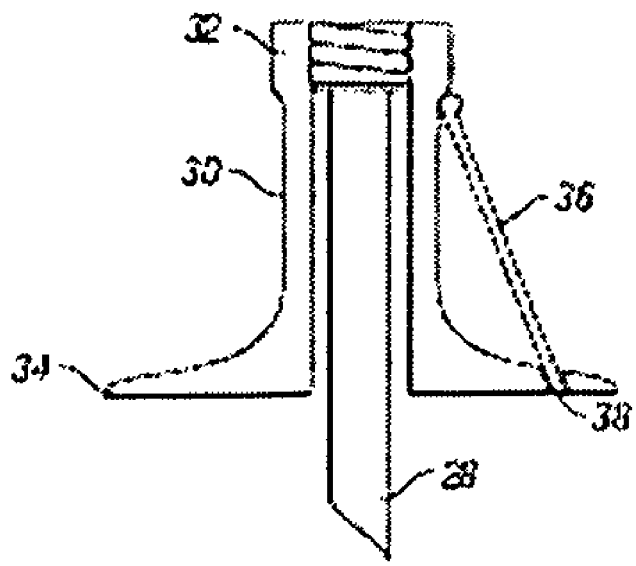
FIG. 2 is a side sectional view of a tip attachment for the syringe of FIG. 1 according to an embodiment of the invention.
Figure 3:
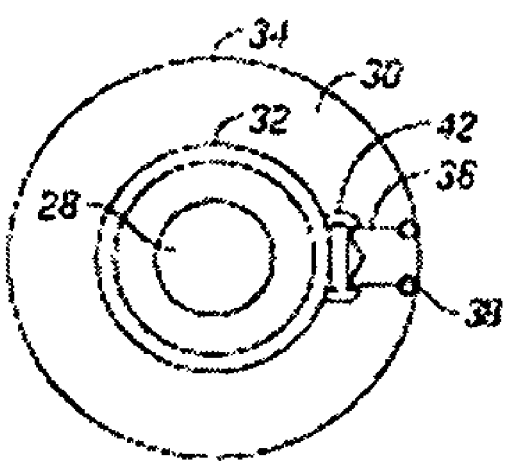
FIG. 3 is a plan view of the proximal side of the tip attachment of FIG. 2.

According to one embodiment illustrated in FIGS. 1-4, the gel/steroid mixture can be injected using a specially designed syringe 10 as best seen in FIG. 1, which has a conventional plunger 12 with a proximal head 14, and a cylinder 16 provided with a proximal flange or handle 18 and a threaded distal end 20 for connection to a needle attachment 22 (see FIGS. 2-3). If desired, the cylinder can have a capacity corresponding to single or multiple injection dosages, e.g. 0.5, 1, 2, 3, 5, 10 or 20 mL, and can be preloaded with a sterile pack 24 of the composition. A removable cap 26 can be provided at the distal end 20, and the syringe 10 provided in conventional sterile packaging (not shown).

The needle attachment 22 shown in FIGS. 2-3 can comprise a central cannula 28 and an outer casing 30 secured thereto. The needle attachment 22 can be provided with a proximal head 32 that can be threaded for connection to the distal syringe tip 20. The casing 30 can be made of an injection molded polymer or other suitable material and can extend coaxially from the base of the cannula 28 to a distal foot 34, which has an enlarged transverse diameter or other cross section, such as, for example, 2 or 3 cm. The foot 34 presents a planar surface or edge from which the distal end of the cannula 28 extends a predetermined distance corresponding to the desired depth of injection. The needle attachment 22 can also be provided with a cap or end enclosure such as a dome (not shown) releasably secured to the foot 34 to facilitate sterile packaging and protect personnel from exposure to the tip of the cannula 28 during transport, storage and preparation for use.

Figure 4:
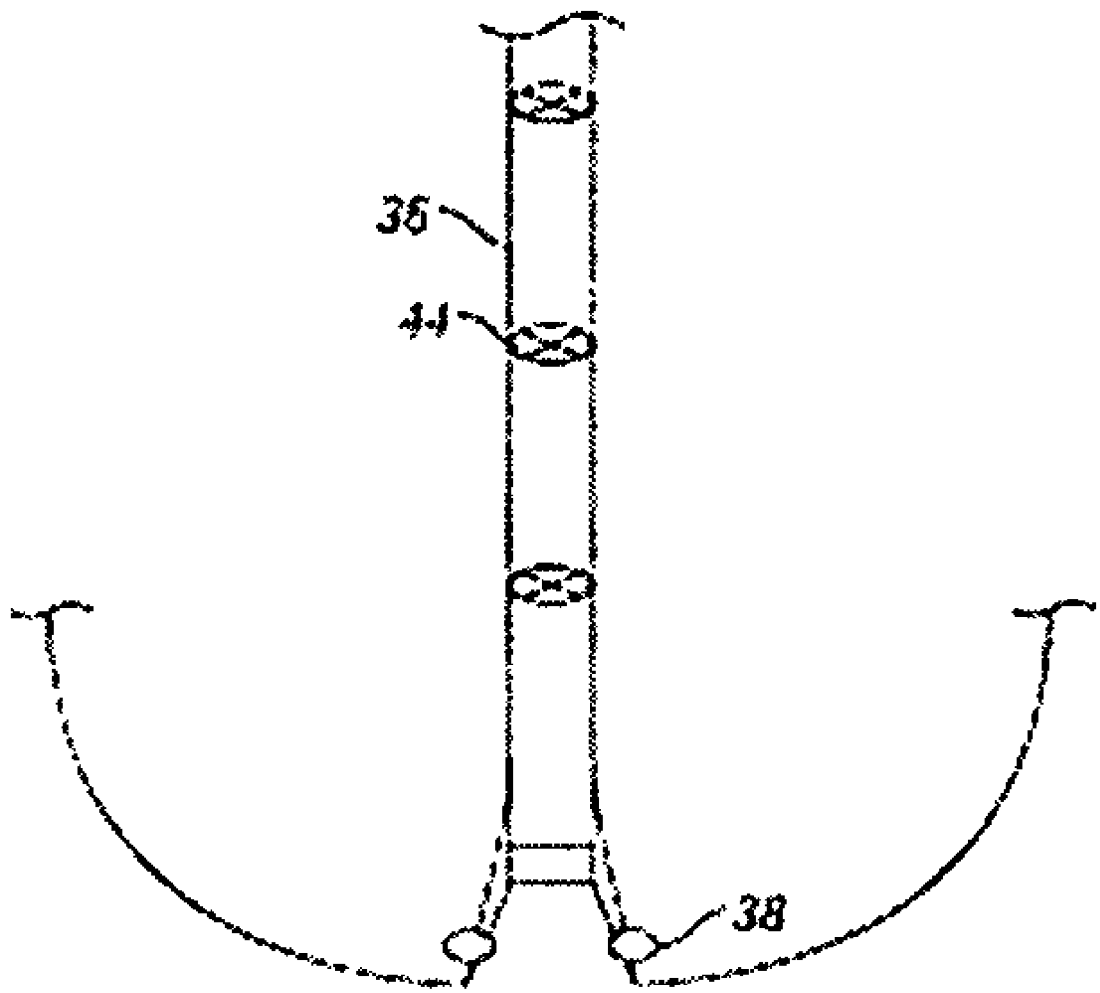
FIG. 4 is an enlarged schematic of a measuring arm seen in the tip attachment of FIGS. 2 and 3.

In one embodiment, the needle attachment 22 can also be provided with a pivotable lateral arm 36 secured to foot 34 via hinge 40. A free end of the arm 36 can be releasably secured to a proximal end of the casing 30 at catch 42. As best seen in FIG. 4, the arm 36 can be provided with graduated markings for distance from the perimeter of the foot 34 and/or the axis of the cannula 28.

In an embodiment, the syringe 10 and needle attachment 22 can be packaged separately or together as part of a kit. If desired, the needle attachment 22 can be packaged or supplied as a set, together with or separately from the syringe, containing an array of the needle attachments to provide a range of different injection depths, foot diameters, and arm lengths in various permutations or combinations that might be used by an operator for a typical procedure with different skin thicknesses, wound sizes, etc.

In use, the preloaded syringe 10 of suitable gel/steroid composition and volume can be removed from sterile packaging and the cap 26 removed prior to use. Where a series of needle attachments 22 are provided, the surgeon can select the appropriate size for the desired injection depth, spacing from the wound margin, and spacing between adjacent injection sites. The attachment 22 is threaded onto the syringe 10, and then the safety dome, if present, can be removed and the arm 36 deployed laterally by releasing from the catch 42 and pivoting outwardly at the hinge 38. After excision of the keloid and any reconstructive procedures, the cannula 28 can be inserted at the injection site an appropriate distance from the margin of the wound. If desired, the diameter of the foot 34 and/or the arm graduations 44 can be used to measure the margin-to-injection site spacing and/or the adjacent injection site spacing. The selected injection depth is obtained by inserting the cannula 28 until the foot 34 abuts the adjacent skin or is appropriately spaced from the skin.

Although not intending to be bound by theory, following injection, the carrier is preferably slowly dissolved or degraded and thereby releases the steroid from the matrix over an extended period of time, e.g. 4-6 weeks. The excess non-interstitial steroid suspension can be immediately available for activity upon injection. The fibrotic portion of the therapeutic agent can hold the steroid or other active ingredient in the vicinity of the injection for an extended period of time to prolong the effect of inhibiting the fibroblasts. It is further believed that the mostly inert fibrotic material may also induce a mild inflammatory response drawing macrophages, fibroblast and inflammatory cells to the perilesional area and thereby diverting a significant percentage of these potentially scar-forming cells from the wound margin.

In an embodiment, the composition is injected perilesionally as described above following total excision of the keloid and any reconstruction.

While the invention has been described above in reference to keloid scar treatment and prevention, the composition, device and method of the invention may be used to treat other diseases or conditions without departing from the invention. For example, the invention can be used in general to retard wound healing or cellular growth where delayed release of active biological compounds is desired from an injectable dispersion, such as the treatment or inhibition of hypertrophic scarring, tumor growth inhibition, and the like.

Example 1

An approximately 46-year old male patient of Afro-American background who had previously been treated multiple times by surgical excision, intralesional steroid injection and radiation, was treated according to the invention. The patient presented with severe facial and neck keloids, which had recurred subsequent to multiple previous surgical keloid excisions and conjoint treatments including intralesional steroid injection and radiation. There was massive keloid formation in the left facial region involving the cheek, pendulous in the ear region and the right supraauricular region. Usually, following excision of a recurrent keloid that has been previously unresponsive to conservative therapy, recurrence will begin within 6 to 8 weeks, and by 2-3 months the scar is readily noticeable again. However, following treatment with surgical excision and circumscribed perilesional injection of KENALOG steroid and GELFOAM gel powder at 4:1, the patient showed healing and no keloid recurrence. One month postoperatively the process of epithelialization healing on the left and right sides was apparent. Three months and 12 months postoperatively, there was complete healing without any evidence of recurrent keloids.

Example 2

An approximately 9-10 year old male presented with a cyst on the right supraauricular region which was excised surgically. Approximately one month later, a keloid began forming at the site of the excision. The patient was treated with total keloid excision according to the invention as described in Example 1 using a pressure dressing postoperatively. The patient returned at 2-3 week intervals. At 6 weeks there was no evidence of keloid recurrence and the patient did not thereafter report keloid recurrence following termination of follow up visits.

Example 3

An approximately 35-36 year old male presented with a recurrent keloid in the left neck region. Radiation treatment did not prevent keloid recurrence. Then, the patient was treated with total keloid excision according to the invention as described in Example 1. Two months and 12 months postoperatively, the surgical wound was completely healed without keloid formation.

Example 4

An approximately 12 year old female presented with a spread scar in the right scapular and upper arm posteriorly. Previous surgical excision did not prevent recurrence. Then, the patient was treated with total scar excision according to the invention as described in Example 1, except that pressure dressings were applied and limited movement was prescribed. Over a six week period there was limited wound breakdown that required wound reconstruction. There was severe depression of the adrenal gland function at 2-3 months postoperatively, which was successfully treated by a course of oral methylprednisolone. Three months and 10 months postoperatively, the surgical wound was completely healed with some spread scar formation in the superior scapular region only, and without spread scar formation elsewhere.

The invention is described above in various embodiments for the purpose of illustration only and various changes and modifications will occur to those skilled in the art. It is intended that all variations and modifications within the scope or spirit of the appended claims be embraced thereby.

The invention claimed is:

1. A method, comprising perilesionally injecting adjacent to a wound subcutaneously at a depth of from 2 to 10 mm a composition comprising a corticosteroid, milled absorbable gelatin sponge, and a carrier fluid, wherein the corticosteroid is disposed in the sponge and the sponge is dispersed in an excess of the carrier fluid, wherein the wound is formed by excision of an abnormal scar selected from the group consisting of keloids, hypertrophic scars, and spread scars.

2. The method of claim 1 wherein the injections are serially spaced to circumscribe the wound.

3. The method of claim 1 wherein the injections are spaced from 5 to 30 mm from a margin of the wound.

4. The method of claim 3 wherein adjacent injections are spaced apart by from 1 to 2 cm.

5. The method of claim 3 wherein the adjacent injections have abutting infiltration to circumscribe the wound.

6. The method of claim 1 wherein the wound is formed by total surgical excision of the scar.

7. The method of claim 1 further comprising reconstruction of the excision site in advance of the perilesional injection.

8. The method of claim 1 wherein the corticosteroid comprises triamcinolone, or an addition salt or ester thereof.

9. The method of claim 1 wherein the corticosteroid comprises triamcinolone acetonide.

10. The method of claim 1 wherein the carrier fluid comprises biological saline solution.

11. The method of claim 1, further comprising admixing a suspension comprising the corticosteroid in an excess of water or saline with dehydrated gel sponge powder to hydrate the gel sponge and to dispose the corticosteroid in interstices of the gel sponge.

12. The method of claim 1, wherein the injection uses a syringe comprising a needle wherein the composition is injectable through the needle.

13. The method of claim 12 wherein the syringe further comprises a sleeve associated with the needle and wherein a distal end of the needle extends beyond the sleeve to a distance of from 2 to 10 mm.

14. The method of claim 12 wherein the syringe further comprises a 5-30 mm first lateral spacing element associated with the sleeve.

15. The method of claim 14 wherein the syringe further comprises a 1-2 cm second lateral spacing element associated with the sleeve.

16. A method, comprising:
    forming a wound by surgical excision of an abnormal scar selected from the group consisting of keloids, hypertrophic scars, and spread scars;
    perilesionally injecting through a needle adjacent to the wound a composition comprising a corticosteroid, milled absorbable gelatin sponge, and a carrier fluid, wherein the corticosteroid is disposed in the sponge and the sponge is dispersed in an excess of the carrier fluid;
    wherein the injections are serially spaced to circumscribe the wound;
    wherein the injections are spaced from 5 to 30 mm from a margin of the wound and subcutaneously injected to a depth of from 2 to 10 mm.

17. The method of claim 16 wherein the corticosteroid is selected from free acid and base forms, their corresponding base and acid addition salts and esters, and combinations thereof.

18. The method of claim 16 wherein the corticosteroid comprises triamcinolone or a corresponding addition salt or ester thereof.

19. A method, comprising:
   forming a wound by total excision of an abnormal scar selected from the group consisting of keloids, hypertrophic scars, and spread scars;
   reconstructing the excision site;
   loading a syringe equipped with a needle with an injectable admixture of a corticosteroid suspension comprising an excess of water or saline with dehydrated gel sponge powder to hydrate the gel sponge and to dispose the corticosteroid in interstices of the gel sponge;
   perilesionally injecting the admixture through the needle adjacent to the excision site, wherein the injections are serially spaced to circumscribe the wound, and wherein the injections are spaced from 5 to 30 mm away from a margin of the wound and subcutaneously injected to a depth of from 2 to 10 mm.

20. The method of claim 19 wherein the perilesional injections are intra-operative only.

* * * * *